United States Patent [19]
Lee

[11] Patent Number: 5,821,073
[45] Date of Patent: Oct. 13, 1998

[54] METHOD AND APPARATUS FOR SINGLE STEP ASSAYS OF WHOLE BLOOD

[75] Inventor: Jin Po Lee, Poway, Calif.

[73] Assignee: Syntron Bioresearch, Inc., Carlsbad, Calif.

[21] Appl. No.: 641,163

[22] Filed: May 9, 1996

[51] Int. Cl.[6] ............................ C12Q 1/68; G01N 33/558
[52] U.S. Cl. .............................. 435/7.92; 422/56; 422/57; 422/58; 435/6; 435/287.2; 435/287.8; 435/970; 436/501; 436/514
[58] Field of Search ................................ 435/6, 7.92, 970, 435/287.2, 287.8; 436/501, 514; 422/56, 57, 58

[56] References Cited

U.S. PATENT DOCUMENTS

| | | | |
|---|---|---|---|
| 4,477,575 | 10/1984 | Vogel et al. | 436/170 |
| 4,861,711 | 8/1989 | Friesen et al. | 435/7 |
| 4,883,764 | 11/1989 | Kloepfer | 436/63 |
| 5,132,086 | 7/1992 | Allen et al. | 422/56 |
| 5,384,264 | 1/1995 | Chen et al. | 436/525 |

*Primary Examiner*—David Saunders
*Attorney, Agent, or Firm*—Fish & Richardson P.C.

[57] ABSTRACT

The invention consists of devices for use in assaying fluid test samples for analyte of interest wherein the samples contain or are suspected of containing cells and cellular components. The devices of the invention each include a hydrophilic cell trap for separation of the cellular fraction from the noncellular fraction of the test sample. The latter fraction migrates through porous, absorbent or bibulous membranes of the device which are impregnated with reagents in at least three separate zones comprising a dye zone, a test zone and a control zone. Formation of a distinctive visual pattern in the control zone indicates that the test was competently performed while formation or relative intensity of the visual pattern in the test zone indicates presence or absence of analyte in the test sample. The devices of the invention are particularly suited for assaying ligands in whole blood without prior separation of erythrocytes and other cells from the blood and without need to measure reflectance in the liquid phase. A method for performing the inventive assays is also disclosed.

16 Claims, 3 Drawing Sheets

METHOD AND APPARATUS FOR SINGLE STEP ASSAYS OF WHOLE BLOOD

FIELD OF THE INVENTION

The invention relates to methods and devices for assaying biological fluid samples. In particular, the invention relates to methods and devices for detecting analyte in whole blood samples which do not require separation of the cellular fraction from the sample before the assay is performed.

BACKGROUND OF THE INVENTION

The development of reagent-impregnated capillary membranes for use in assaying various bodily fluids has enabled the production of test devices which are simple to use and produce relatively rapid results (e.g., in as little as 10 minutes or less). Perhaps the most common application for such devices is in the detection of human chorionic gonadotropin as an indicator of pregnancy in humans. Examples of such devices are described in commonly assigned U.S. Pat. No. 5,384,264 as well as in EPO Publication No. 0560411A2, PCT application Ser. No. PCT/GB/00322 and U.S. Pat. No. 4,366,241. In their most simple form, such devices may permit the assay to be performed and results read in a single step; e.g., where the liquid sample (such as urine) is placed onto a bibulous membrane, any analyte of interest therein binds a corresponding ligand, and the results (i.e., formation of a specific complex) are indicated visually in a detection zone separate from the sample loading zone.

While such devices work well for assays of body fluids which typically do not contain relatively large cells (and therefore readily pass through the reagent-impregnated membrane by capillary action or the like), they have not been adaptable to assays for analyte in large cell-containing fluids such as whole blood. Instead, assays for analytes present in whole blood are typically performed on a substantially cell-free plasma or serum fraction and therefore require that the sample be depleted of erythrocytes and other cells before the assay is performed.

A device described in U.S. Pat. No. 5,304,468 ostensibly avoids the need to isolate a plasma or serum fraction from whole blood before assaying for analyte; in particular, glucose. The device (a test strip) described includes opposing sample introduction and test surfaces, the latter of which is impregnated with reagents. Positive or negative results are indicated by a change in reflectance at the test surface which is detected optically. According to the disclosure, detection of the change in reflectance is not affected by the presence of erythrocytes in the test sample such that whole blood samples may be applied to the sample introduction surface. However, because results are measured in changes in reflectance, an optical measuring device is required to perform assays using the disclosed device.

SUMMARY OF THE INVENTION

The invention consists of devices and methods for performing single-step assays for analyte in cell-containing fluid samples without the need to separate a non-cellular liquid fraction from the cells in the sample before the assay is performed. Further, the invention does not require use of hydrophobic films to repel cellular components in the sample or subsequent washing steps to eliminate the repelled components from the assay device. In addition, the results of assays performed according to the invention may be read visually without use of separate measuring equipment and without regard to reflectance of the test sample. Thus, performance of assays according to the invention requires only that the user introduce the requisite amount of test sample (preferably, whole blood) into the device of the invention then observe any color changes or the like which appear shortly thereafter in a detection zone of the device.

To this end, the device of the invention includes a cell trap at the point of entry for test sample into a hydrophilic sample introduction membrane. The trap, which is preferably a layered, hydrophilic mesh having pores of effective diameter less than the expected diameter of the cells in the analyte sample, is disposed in fluid communication with the sample introduction membrane. Thus, in use, only the fluid fraction of the test sample passes from the cell trap into the sample introduction membrane. In turn, fluid entering the sample introduction membrane passes through the membrane into reagent-impregnated dye zone, then into test and control zones. In the most preferred embodiment of the device of the invention, visually detectable particulate dyes (such as sols of metal-containing inorganic compounds) are used to derive positive or negative test results.

The device of the invention may be of any suitable shape or form, including test strips and cassettes which enclose the various components of the device.

According to the method of the invention, a small quantity of test sample (preferably, whole blood) is pipetted or applied dropwise or applied elsewise (e.g., by direct contact with a punctured finger) into a cell trap. Binding of any analyte present in the sample (not bound to the membranes of the separated cellular components) with one or more specific ligands causes formation of specific visual pattern indicative of the test result.

The invention may be used to detect any analyte present in fluid sample (e.g., soluble antigen in whole blood) for which at least one specific ligand (binding partner) is known (e.g., a polyclonal or monoclonal antibody). The invention is especially useful for detection of monoepitopic and polyepitopic antigens and antibodies associated with infectious and noninfectious pathologies, as well as physiological compounds and drugs. Although of particular use in assaying whole blood samples, the device of the invention may be used to assay other liquid samples, particularly samples in which cells or other interfering particles of comparable size are known to occur.

BRIEF DESCRIPTION OF THE DRAWINGS

Like numerals refer to like elements in the drawings.

DETAILED DESCRIPTION OF THE INVENTION

1. Definitions

Figure 1:
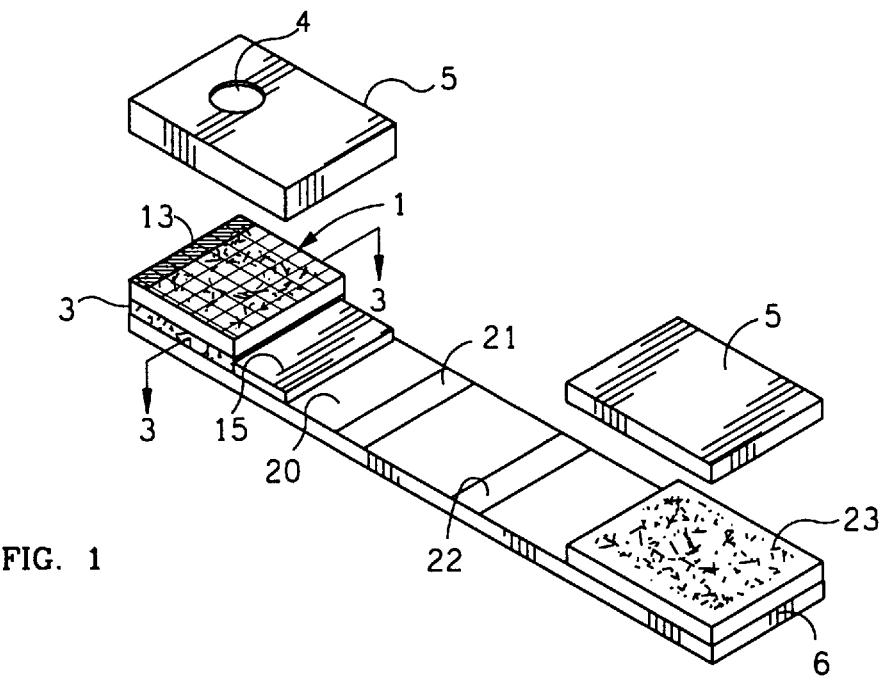
FIG. 1 is an exploded view of a test strip of the invention.

For ease of understanding, the following definitions will apply throughout this description:

a) Analyte

A molecule or compound containing one or more binding sites (e.g., epitopes), i.e., those points at which another molecule or compound will bind.

b) Ligand and Binding Pair

Molecules or compounds which bind to particular binding sites on analyte to form a "binding pair". Any analyte/ligand binding pair of interest may be utilized in the invention. Structurally, ligands may include proteins, peptides, carbohydrates, polysaccharides, nucleic acids, oligonucleotides, haptens and combinations thereof. Functionally, the ligands may include, but will not be limited to, antibodies, antigens (e.g., microbial antigens, prostate specific antigen), hormones (e.g., thyroid stimulating hormone), drugs, enzymes, allergens, as well as fragments, modifications and combinations thereof. Those of ordinary skill in the art will be familiar with, or may readily identify, such ligands and corresponding binding pairs.

c) Test Sample

A fluid suspected of containing analyte of interest for which a particular assay will be specific.

d) Label

A molecule or compound which directly or indirectly mediates the formation of a signal (such as a color change) which is used in assay to indicate the presence, absence or concentration range of analyte of interest in a test sample. Labels may include enzymes, fluorescors, liposomes, erythrocyte ghosts, polymer microcapsules, color polymer particles (latex), and will preferably include sols of metal-containing compounds.

e) Metal Label

Labels of metal-containing sols; i.e., metal or metal compounds such as metal oxides, metal hydroxides, metal salts, metals or metal-containing compounds mixed with polymers or coated onto polymer nuclei. These metal labels may include dry forms of any of the above-named metal or metal compound sols, and will preferably include colloidal gold in dry form.

f) Complex

Depending on the context in which it is used, "complex" shall mean any multimolecular complex formed by analyte and one or more ligands, or by labeled ligand and immobilized ligand. In a sandwich-type immunoassay, e.g., the following complexes occur: analyte/labeled ligand duplex first produced in the assay ("first complex") and analyte/labeled ligand/immobilized ligand triplex formed second in the assay ("second complex").

g) Cellular Components

Refers to cellular membranes and intracellular structures such as mitochondria and nuclei.

h) Noncellular fraction

Refers to the liquid phase of a test sample including any analyte present therein and cellular components not captured in the cell trap of the devices of the invention.

2. Preferred Embodiments of the Devices of the Invention

Although the devices of the invention may take any shape or configuration which includes the material elements of the invention, the preferred configurations of the device will be test strips and cassettes enclosing internal components of the inventive devices. Thus, the devices of the invention are described in this disclosure as test strips and cassette-type devices, although the invention will be understood not to be limited to these particular configurations.

A test strip constructed in accord with the invention is shown in FIG. 1. On the left-hand side of the FIGURE, cell trap 1 is shown as a layered mesh overlying sample introduction membrane 3. Access to cell trap 1 for application of test sample is obtained through window 4 in cover 5. Cover 5 is a thin layer or film of hydrophobic material extending over all or a part of the upper surface of the test strip. Although cover 5 may be omitted from the test strip, it serves to help accurate sample application through window 4, to protect cell trap 1 from contamination and to prevent separation of cell trap 1 from sample introduction membrane 3. Thus, inclusion of cover 5 in test strips of the invention is preferred.

Figure 2:
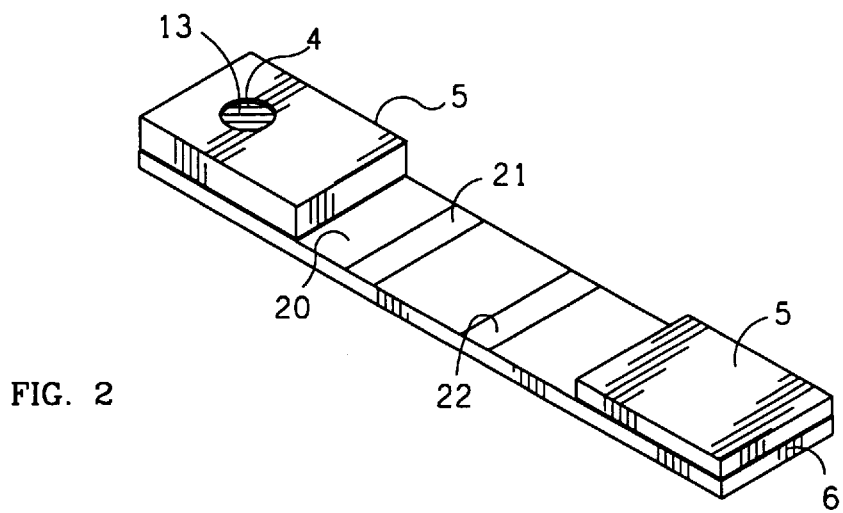
FIG. 2 is a perspective view of a test strip of the invention.

Opposing cover 5 is a thin, hydrophobic substrate 6. Substrate 6 serves as a rigid support for all functional components of the test strip described below and as a barrier to passage of fluid out of the test strip through the bottom surface of the device. Suitable materials for use as cover 5 and substrate 6 include cellulose derivatives, polyvinyl and polyacrylic compounds as well as other solid polymers, which may be used to form cover 5 and substrate 6 or may be used as a coating where the cover or the substrate is composed of a different material (such as paper). The preferred positioning of cover 5 and substrate 6 on the test strip is shown in FIG. 2.

Figure 3:
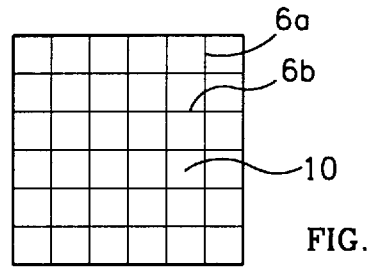
FIG. 3 is an enlarged sectional view taken on line 3—3 of FIG. 1 through the layer comprising cell trap 1.

The structure of cell trap 1 is shown in further detail in FIG. 3. As shown in FIG. 3, cell trap 1 consists of multiple layers of fibers (represented by fibers 6a and 6b) oriented in overlapping cross-section to form a mesh (underlying layers of overlapping fibers are shown in phantom). The pores formed by the overlapping fibers must not exceed, and will preferably be less than, the expected diameter of the erythrocytes or other cells in the test sample. To facilitate filtration, pore sizes in upper fiber layers of the cell trap may be different from the pore sizes in the underlying fiber layers. In this disclosure, the smallest pore size in certain layers of the cell trap is referred to as effective pore size of the cell trap. For human erythrocytes, the average diameter is 7.7 microns and the average thickness is about 2 microns. For ease of understanding, the cells to be separated in cell trap 1 are referred to in this disclosure as erythrocytes, although it will be understood that the invention is not limited to use with test samples containing erythrocytes.

As shown in FIG. 3 (not drawn to scale), each pore (represented by pore 7) of cell trap 1 has effective size somewhat less than the size of trapped cells (represented by cell 10 in FIG. 3). The fibers which form the boundaries of each pore are tightly woven so as to not deform on exposure to test sample; i.e., so as not to enlarge the pore size. For efficient cell separation, it is generally preferred that the effective pore size of cell trap 1 be at least 10% smaller than the expected diameter of the cells to be trapped. Within the scope of the invention, the test sample may contain heterogenous cell populations. In such cases, the effective pore size is preferred to be at least 10% smaller than the diameter of the smallest cells in the test sample. Smaller pores may also be used to enhance the ability of the inventive devices to trap cellular components as well as whole cells. In all cases, the pore size should not be so small that the passage of the noncellular fluid fraction of the test sample is impeded from flowing through the pores to enter sample introduction membrane 3.

Those of ordinary skill in the art will appreciate that erythrocytes or other cells present in the test sample may not be of the expected size and, where smaller than expected, could pass through a pore of cell trap 1. Thus, to enhance the trapping capacity of cell trap 1, at least 2 and preferably more than 3 layers of overlapping fibers will be stacked in transverse orientation from layer to layer to form cell trap 1.

Further, although uniformly overlapping fibers are shown in FIG. 3, those of ordinary skill in the art will appreciate that more randomly oriented fibers may be used in cell trap 1. In such a structure, not all of the pores will be of uniform size. It is therefore possible that erythrocytes in an analyte sample applied to cell trap 1 will pass through one or more layers of overlapped fibers. Each layer of overlapping fibers in cell trap 1 should be transversely oriented so cells which are not trapped in a superficial layer are trapped in deeper layers of the trap. To this end, at least three layers of overlapping fibers are preferably included in cell trap 1. In order for the noncellular fluid fraction of the test sample to more readily soak through cell trap 1 into sample introduction membrane 3, cell trap 1 will preferably have a total thickness of between 0.1 millimeters and 3 millimeters. The surface area available for application of the test sample through window 4 of cell trap 1 (FIG. 1) will vary depending on test sample volume and on the method of application; for testing most whole blood samples according to the invention, a surface area between about 3 mm$^2$ and 25 mm$^2$ is expected to be adequate.

It is not necessary that the fibers of cell trap 1 have any particular charge or individual thickness for trapping of erythrocytes. However, to assist the noncellular fraction of analyte sample in passing through cell trap 1 to sample introduction membrane 3, it is desirable that cell trap 1 be somewhat hydrophilic so fluid is not repelled from soaking through the pores of the trap. Any fibrous material having the characteristics described may be used as cell trap 1. Conveniently, preformed pads or strips of layered nylon or cellulosic filter materials (such as nitrocellulose) may be used.

Returning to FIG. 1 sample introduction membrane 3 is disposed beneath, and in fluid communication with, cell trap 1. In this disclosure, "fluid communication" refers to structures which are in contact with, but not necessarily affixed to, one another. Preferably, sample introduction membrane 3 is more porous than cell trap 1 and is also somewhat more hydrophilic to facilitate unidirectional flow of fluid from cell trap 1. Alternatively, the material used to form cell trap 1 may also form sample introduction membrane 3.

As shown in FIG. 1, sample introduction membrane 3 is disposed entirely beneath cell trap 1. However, once the entire structure of the test strip of FIG. 1 has been described, those of ordinary skill in the art will recognize that sample introduction membrane 3 may be offset beneath cell trap 1 in the direction of flow toward reagent-impregnated membrane 20. In all embodiments of the inventive devices, sample introduction membrane 3 and cell trap 1 should be in fluid communication.

Where sample introduction membrane 3 is a separate material of greater porosity than cell trap 1, any absorbent, porous, bibulous or otherwise hydrophilic material may be used to form the membrane. Examples of such materials are well-known in the art and include tightly woven paper, nitrocellulose, fiberglass and porous plastics, such as high molecular weight polypropylene and acrylonitrile. Preferably, the porosity of the material chosen will be sufficient to absorb the fluid component of about 20 to 40 microliters of blood in a few seconds. As described further below with respect to a method of using the test strip of the invention, buffer is preferably also applied during the assay to the proximal end of sample introduction membrane 3 to assist in propelling the relatively small volume of analyte sample through the various membranes of the test strip. To this end, a buffer zone 13 is shown in phantom in FIG. 1.

It will be appreciated that buffer is not critical to the performance of all assays which may be performed using the devices of the invention; i.e., all fluid flow may be provided by liquid derived from the test sample. However, the use of buffer will generally minimize the volume of test sample needed and increase the speed that the assay may be completed.

Sample introduction membrane 3 is in fluid communication with dye impregnated membrane 15. More particularly, one or more labeled ligands (e.g., antibody or antigen) is bound by use of soluble aminosilanes or other suitable binding means well-known to those of skill in the art to a porous, absorbent or bibulous membrane. The preferred membrane material is a fiberglass such as that which is marketed under the trade names "MANNIWEB" or "MANNIGLAS" by Lydall, Inc. Other suitable materials include polyethylene or nitrocellulose pads and strips; means for binding ligands to these materials are well-known in the art. Alternatively, dye impregnated membrane 15 may be a part of sample introduction membrane 3. However, to minimize backwash of labeled ligand into sample introduction membrane 3, it is preferable that dye impregnated membrane 15 be a separate structure, most preferably a fibrous material (such as the fiberglass described above) having fibers oriented generally in the direction of the reagent impregnated membrane described below.

The labeled ligand will be prepared according to the means known in the art. For purposes of producing a clearly visible reaction, labels of metal-containing sols are preferred, with labels of colloidal gold or selenium being most preferred. An example of a suitable product is colloidal gold available from Janssen Life Sciences Products. These colloidal metals will produce distinctive visual patterns without addition of further reagents; however, fluorescors (such as fluorescein) and enzymes (such as those identified in U.S. Pat. No. 4,275,149, incorporated to that extent herein), may also be used. To maximize contact of test sample with labeled ligand, the area occupied by the latter (test zone 21 and control zone 22) will preferably extend from one side of the membrane to the other.

A first immobilized ligand is immobilized on reagent impregnated membrane 20 in test zone 21 (which lies proximal to dye impregnated membrane 15). This will be the location of the sample test region. Reagent impregnated membrane 20 is preferably a porous strip coated with gelatin to enhance the life of the strip and clarity of any visible reactions produced in the test. The first immobilized ligand may be immovably bound to reagent impregnated membrane 20 by means known in the art, including covalent bonding or attachment to an insoluble protein-coated surface (see, e.g., U.S. Pat. No. 4,200,690, the disclosure of which is to that extent incorporated herein).

Preferably, the area occupied by first immobilized ligand will have the shape of a bar or an oval extending from side to side of reagent impregnated membrane 20 at test zone 21. Use of a simple, unidirectional configuration such as a bar avoids the need for the user to determine if a more complex shape (such as a "+" or a "−") has been sufficiently formed to indicate a particular result. Further, use of a simple shape overcomes the impact of leading edge effects and makes visual interpretation of results easier for the user.

Distal to dye impregnated membrane 15, a second immobilized ligand is located in control zone 22. The second immobilized ligand should have specific affinity for at least one of the labeled ligands. Immobilization of the second immobilized ligand may be performed using same methods described with respect to binding of the first immobilized ligand above. For ease of comparison, the shape and orientation of the control zone 22 should be similar to the shape and orientation of the test zone. Those of ordinary skill in the art will appreciate that the positions of test zone 21 and control zone 22 on reagent impregnated membrane 20 may be reversed so the former is distal, and the latter is proximal, to dye impregnated membrane 15.

Absorbent pad 23 is in fluid communication with reagent impregnated membrane 20 and serves as a reservoir for excess fluid as well as a pump to provide uni-directional fluid flow along reagent impregnated membrane 20. To the latter end, absorbent pad 23 preferably overlaps reagent impregnated membrane 20 at its distal end just distal to control zone 22. Those of skill in the art will appreciate that some embodiments of the invention may not include the absorbent pad. Its function may be fulfilled, e.g., by extended distal end of the reagent impregnated membrane 20. However, for optimum performance the embodiments incorporating absorbent pad are preferred.

Instructions for use of the test strip may be printed onto the cover or onto the packaging of the test strip and/or will be printed in literature to be packaged with the test strip. Preferably, the test strip will be part of a kit which may be composed of the test strip, instructions for its use, a desiccant packet, a capillary device for measuring test sample, buffer, a pipette for measuring buffer, and a reaction chamber, such as a cup into which buffer and the buffer introduction zone of the test strip are placed after analyte sample has been applied to the test strip. Components of such a kit for use in performing an assay procedure (e.g., excluding printed instructions) are preferably to be sealed in one or more air-tight packages, such as foil packets.

3. Alternative Embodiment: Container Device

Figure 4:
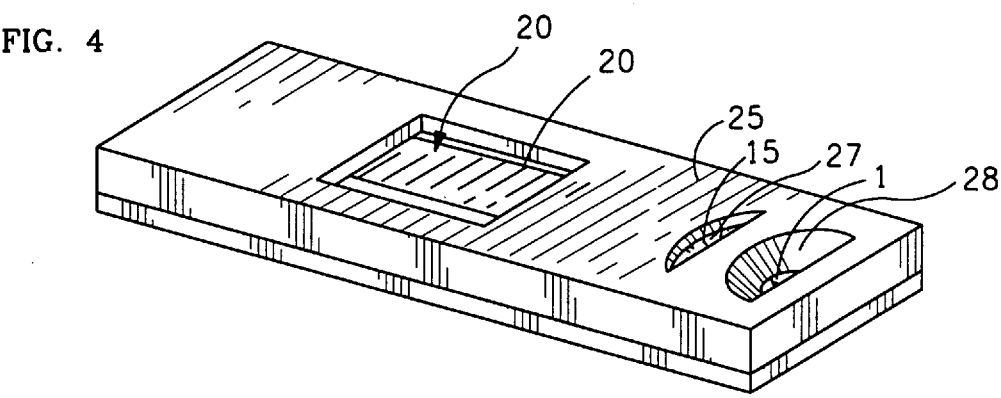
FIG. 4 is a perspective view of a cassette device of the invention.

Alternatively, all of the components described with respect to the test strip of the invention (except cover 5 and substrate 6) may be encased in a fluid-tight housing composed of a solid plastic cover 25 which fits tightly over solid plastic base 26 as shown in FIG. 4. A port 27 for application of test sample onto cell trap 1 is disposed through cover 25. In the preferred embodiment, a port 28 for application of buffer to the device is also disposed through cover 25. However, other embodiments wherein the test sample and the buffer are applied via the same port are also within the scope of this invention. A display port 29 is also disposed through cover 25 for viewing of reagent impregnated membrane 20.

Figure 5:
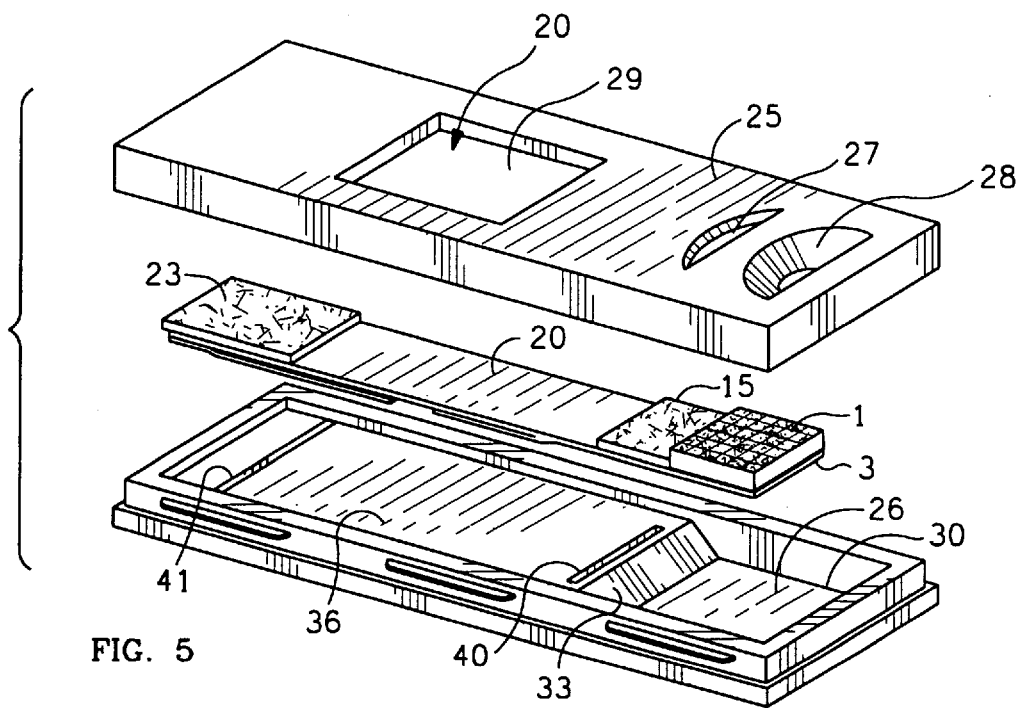
FIG. 5 is an exploded view of a cassette device of the invention.

A particularly preferred cassette design for use in the invention is disclosed in commonly assigned U.S. Pat. No. 5,384,264, the disclosure of which is to that extent incorporated herein by this reference. Briefly, a cassette device constructed in accord with the 5,384,264 patent and this disclosure is shown in exploded view in FIG. 5. In this view, it can be seen that base 26 is divided into two distinct regions. The first is depression 30, which is defined by bottom surface 31, sidewalls 32 and slope 33. In a preferred embodiment, a vertical bar 34 (not shown) extends downward from cover 25 into depression 30 just adjacent to slope 33 to hold dye impregnated membrane 15 in place along slope 33.

The second region of substrate 26 begins at the top of slope 33 and consists of an extended surface forming platform 36 parallel to and extending away from depression 30. Fluid gully 40 is preferably included at the proximal end of platform 36 as an additional reservoir for excess liquid. Platform 36 may extend the length of substrate 26 from slope 33, or it may stop just short of the distal end of substrate 26, thus leaving room for a second fluid gully 41 to collect excess liquid. Reagent impregnated membrane is disposed along most of the length of platform 36 (below the opposing location of display port 29), while absorbent pad 23 is disposed at the distal end of platform 36 and may extend over fluid gully 41. A desiccant tablet may be placed into fluid gully 41. Desiccant provides low humidity conditions necessary for preservation of reagents during the shelf life of the device. Alternatively, a desiccant tablet or a desiccant packet may be included in an air-tight protective pouch wit the device.

4. Method for Use of the Inventive Devices

Test sample may represent any body fluid, including blood, urine, lymph, intraperitoneal fluid, crude tissue extract or homogenate, derived from a fetus, neonate, juvenile or adult subject, but will preferably be whole capillary or venous blood. For most applications, about 5 microliters to 50 microliters of test sample will suffice for use in the invention, preferably 20 microliters to 30 microliters.

The method of the invention is performed by applying test sample to the cell trap of a device (test strip or cassette) constructed according to the invention. For test samples which contain (or are suspected of containing) cellular components, sufficient time is provided for separation of the cellular and noncellular fractions, usually about 60 to 120 seconds. After the above step is completed, buffer is added through the buffer zone or port of the device.

The volume of buffer added must be limited to avoid washing out of the test sample. In general, less than five drops (and preferably three full drops) of buffer will be sufficient for use in propelling test sample along the membranes of the testing device. Suitable buffers include any pharmaceutically acceptable aqueous buffer which will not react with the test sample or its components. Those of ordinary skill in the art will be familiar with, or may readily identify, such buffers which include saline, Ringer's solution and the like. Buffer may be added to the buffer port dropwise (for cassette-type device) or by placing the requisite volume of buffer into a reaction container (cup) and then immersing the buffer zone of the test strip therein (for test strip embodiment of the invention). Both the test sample and buffer should be at room temperature (about 15° C. to 30° C.) when applied to the device.

After application of test sample and buffer, results may be read in about 10 minutes. In the embodiments that do not require use of buffer, the results may develop more slowly depending on the rate of flow of the noncellular fraction of the test sample through the membranes of the testing device. Without the use of buffer, results are read at about the same time that a band appears in the control zone. If no band appears, or if the control band is neither distinct nor fully formed, the assay should be regarded as incompetent to indicate the presence or absence of analyte in the test samples and should be performed again.

More specifically, in a sandwich-type assay, analytes of interest in the test sample, if present, will bind the labeled ligand in the dye zone to form a first complex. The first complex and unbound labeled ligand will mix with the test sample and be carried along therewith by capillary action ("wicking") through the dye impregnated membrane (dye zone) into the reagent impregnated membrane of the device.

Sample will pass through the reagent impregnated membrane bringing the first complexes, if any, into contact with the unlabeled ligand immobilized on the reagent impregnated membrane to bind therewith to form a second complex of labeled ligand-analyte-immobilized ligand. If the second complex is formed, a visible color pattern will appear in the test zone.

Labeled ligand not bound to analyte in the test sample will continue migration by wicking into the control zone to contact the ligand immobilized there. The labeled ligand will bind the immobilized ligand in the control zone to form a third complex, and thus will be captured in the control zone. Within the scope of this invention, the labeled ligand forming the complex in the control zone may be the same as the labeled ligand forming the first and second complexes, or it may be a different labeled ligand. The ligand immobilized in the control zone should have specific affinity for the labeled ligand intended to form the third complex. Formation of the third complex is indicated by a visible pattern in the control zone.

Besides sandwich immunoassay method, other assay methods may be implemented in the devices of the invention. These methods may include competition and inhibition assays.

In a competition assay, analyte and labeled ligand have similar affinity properties and compete for binding with immobilized ligand. Thus, in absence of analyte the pattern (e.g., band) in the test zone will be of maximum intensity. If present, the analyte will bind to immobilized ligand and thus prevent the labeled ligand from getting captured in the test zone. Thus, the intensity of the test band will be reduced depending on the concentration of analyte in the test sample.

In an inhibition assay, analyte and immobilized ligand in test zone will have affinity for labeled ligand. In absence of analyte, the labeled ligand will be captured by immobilized ligand, and a visible pattern will form in the test zone. If present, analyte will bind labeled ligand and thus will prevent it from binding to immobilized ligand in the test zone. The resulting intensity of the test band will be reduced depending on the concentration of analyte in the test sample.

All assay methods within the scope of this invention may be designed for reading of test results in one of the two modes: visual identification mode and comparison mode. In visual identification mode, positive or negative result (presence or absence of analyte above certain concentrations) is determined by visibility of certain pattern or color in the test zone. The pattern in control zone serves only as internal control of functionality of the device. In comparison mode, positive or negative result is obtained by visually comparing the intensities of the patterns formed in test and control zones. Thus, in the latter case, control zone pattern serves both as internal quality control and as a reference standard for reading of results in comparison mode.

Figure 6:
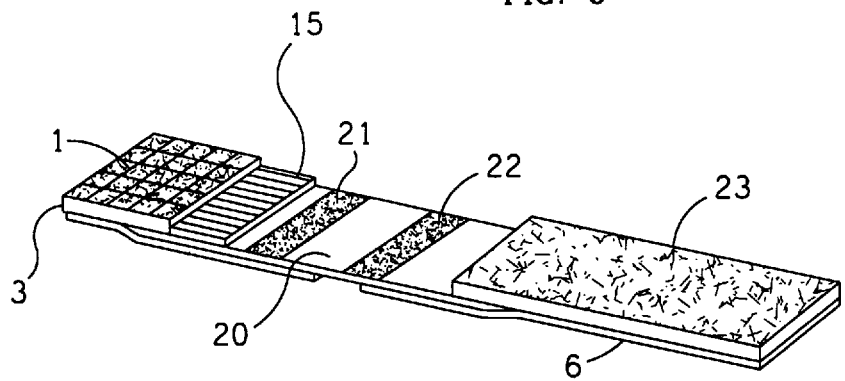
FIG. 6 is a perspective view of a test strip of the invention (without cover) showing a visual result in the test zone for the presence of analyte in a sample.
Figure 7:
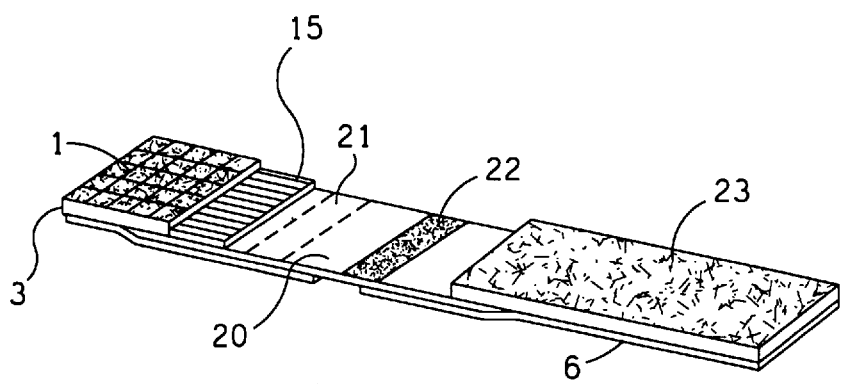
FIG. 7 is a perspective view of a test strip of the invention (without cover) showing an alternative visual result in the test zone for the presence of analyte in a sample.

An example of a test result in a visual identification mode is shown in FIG. 6 and FIG. 7. In this case, as shown in FIG. 6, a positive result is indicated by formation of similar horizonal bars in test zone 21 and in control zone 22. In contrast, as shown in FIG. 7, a negative result is indicated by a distinguishable horizontal bar appearing only in control zone 22.

Other control or comparative result signals may be provided, including signals which indicate whether an invalid result is obtained, by similar means known to those skilled in the art (see, e.g., the signal system described in European Patent Application No. 8611367.0 [Publication No. 0217 403 A2]).

The present invention is applicable to devices and procedures for detection of a wide variety of analytes. As examples of types of analytes, the following may be mentioned: proteins and protein derivatives, including antibodies, immunoglobulins, hormones, enzymes, and peptides; infectious agents, including bacteria, viruses, fungi, mycoplasma, parasites and products and components thereof; drugs, including therapeutic drugs and drugs of abuse; and cancer markers. Particular examples are antibodies against HIV, antibodies against $H.$ $Pylori$, antibodies against hepatitis C virus, human chorionic gonadotropin, estradiol, thyroid-stimulating hormone, prostate specific antigen, hepatitis B surface antigen, myoglobin, and immunoglobulin E.

Examples illustrating the invention are provided below, but should not be taken to limit the scope of the invention, which is defined by the appended claims. Standard abbreviations (e.g., "h" for hours) and units of measurement (e.g., "ml" for milliliters) are used in the examples.

EXAMPLE I

DETECTION OF ANTI-BACTERIAL ANTIBODIES IN HUMAN BLOOD

A test sample of whole capillary blood was obtained from an adult human subject utilizing conventional specimen collection techniques by fingertip puncturing. Approximately 20 μl of blood was applied by direct contact with the surface of the cell trap of a test strip constructed in accord with the invention to include a polyepitopic microbial antigen reagent (of $H.$ $pylori$) reactive with all isotypes of human antibodies against $H.$ $pylori$. After 90 seconds, three full drops of buffer (saline) were applied to the buffer zone of the test strip by dipping the test strip into a cup containing three drops of buffer. The test sample and buffer applied to the test strip were both at a temperature of about 15°–30° C. at the time of application.

After applying buffer, the test strip was allowed to rest at room temperature in the buffer cup for 10 minutes. Two bands of color were observed in the detection and control zones of the strip, indicating a competent test (indicated by the appearance of the control band in the control zone) positive for anti-$H.$ $pylori$ antibodies in the test sample (indicated by the appearance of a colored band in the detection zone). The test strip and any unused test sample were then disposed of according to conventional biological waste handling techniques.

EXAMPLE II

DETECTION OF PROSTATE SPECIFIC ANTIGEN IN WHOLE BLOOD

An test sample of whole venous blood was obtained from an adult human subject utilizing conventional blood specimen collection techniques; i.e., an intravascular syringe. Approximately 20 μl of the test sample was pipetted onto the cell trap of a container device constructed in accord with the invention to include a monoclonal antibody reagent specific to human prostate specific antigen. After 90 seconds, three full drops of buffer (saline) were added dropwise by pipette to the cell trap. The test sample and buffer applied to the test strip were both at a temperature of about 15°–30° C. at the time of application.

After applying buffer, the device was left at room temperature on a flat, horizontal surface for 10 minutes. Two bands of color were observed in the detection and control zones of the strip, indicating a competent test (indicated by the appearance of the control band in the control zone) positive for human prostate specific antigen in the test sample (indicated by the appearance of a colored band in the detection zone). The device and any unused test sample were then disposed of according to conventional biological waste handling techniques.

The invention having been fully described, modifications to the embodiments described will become apparent to those of ordinary skill in the art. All such modifications are regarded as being part of the invention and within the scope of the appended claims.

The invention claimed is:

1. A device for assaying fluid test samples containing cells and cellular components as well as being suspected of containing an analyte of interest comprising:

a hydrophilic cell trap having a thickness of 0.1 mm to 3 mm, consisting of at least three layers of overlapping fibers having an effective pore size from fiber to fiber no larger than the smallest expected diameter of all cells in the test sample;

a hydrophilic sample introduction membrane in fluid communication with the cell trap;

a label impregnated membrane in fluid communication with the sample introduction membrane;

a reagent impregnated membrane in fluid communication with the label impregnated membrane having a control zone and at least one test zone;

at least one soluble labeled ligand in the label impregnated membrane, capable of binding analyte or competing with analyte for binding with immobilized ligand in the test zone;

an immobilized ligand in the test zone, capable of binding analyte or labeled ligand;

an immobilized ligand in the control zone, capable of binding at least one of the labeled ligands;

wherein each of the sample introduction membrane, dye impregnated membrane and reagent impregnated membrane are disposed on a hydrophobic substrate.

2. The device according to claim 1 wherein the effective pore size from fiber to fiber in at least one layer does not exceed 8 microns.

3. The device according to claim 1 wherein the effective pore size from fiber to fiber in at least one layer does not exceed 2 microns.

4. The device according to claim 1 wherein the cell trap is disposed over the sample introduction membrane.

5. The device according to claim 1 wherein the sample introduction membrane has an effective pore size equal to or greater than that of the cell trap.

6. The device according to claim 1 wherein the cell trap is composed of hydrophilic materials selected from the group consisting of cellulose derivatives, nylon, fiberglass and their combinations.

7. The device according to claim 1 wherein the sample introduction membrane is composed of hydrophilic materials selected from the group consisting of cellulose derivatives, nylon, fiberglass and their combinations.

8. The device according to claim 1 further comprising a hydrophobic cover overlying the cell trap and membranes of the device wherein the cover has a window therethrough disposed over the cell trap.

9. The device according to claim 1 wherein the substrate is a strip.

10. The device according to claim 8 wherein the substrate and cover are formed of a biocompatible solid, wherein the substrate and cover form a housing enclosing the cell trap and membranes of the device.

11. The device according to claim 10 further comprising an absorbent material disposed in fluid communication with the reagent-impregnated membrane.

12. The device according to claim 1 wherein the cell trap and membranes of the device are arranged in a strip for flow of test sample from the cell trap through the sample introduction membrane, label impregnated membrane and reagent impregnated membrane.

13. The device according to claim 1 wherein the label of the label impregnated membrane is selected from the group consisting of enzymes, liposomes, erythrocyte ghosts, polymer microcapsules, color polymer particles (latex), sols of metal, and sols of metal-containing compounds.

14. The device according to claim 13 wherein the label is colloidal gold.

15. The device according to claim 1 where the ligands are selected from the group consisting of antigens, antibodies, hormones, enzymes, peptides, proteins, nucleic acids, oligonucleotides, glycoproteins, carbohydrates, polysaccharides and combinations thereof.

16. A method for assaying fluid test samples containing cells and cellular components as well as being suspected of containing analyte of interest comprising:

applying a test sample to the cell trap of the device of claim 1;

detecting a pattern in the control zone; and, detecting a pattern in the test zone, wherein a detectable pattern in the control zone indicates that a competent assay was performed, and a detectable pattern in the test zone indicates the presence or absence of analyte in the test sample.

* * * * *